(12) United States Patent
Muto et al.

(10) Patent No.: US 8,167,897 B2
(45) Date of Patent: May 1, 2012

(54) SURGICAL INSTRUMENT ASSEMBLY

(75) Inventors: Rudolph Muto, Andover, MA (US);
Thomas M. Prezkop, Andover, MA (US)

(73) Assignee: Thomas M. Prezkop, Andover, MA (US)

( * ) Notice: Subject to any disclaimer, the term of this patent is extended or adjusted under 35 U.S.C. 154(b) by 107 days.

(21) Appl. No.: 12/002,941

(22) Filed: Dec. 18, 2007

(65) Prior Publication Data

US 2009/0157110 A1   Jun. 18, 2009

(51) Int. Cl.
*A61B 17/32* (2006.01)

(52) U.S. Cl. ........................................... 606/167
(58) Field of Classification Search ............... 606/167, 606/169, 170, 171, 172; 30/151, 161, 162, 30/335

See application file for complete search history.

(56) References Cited

U.S. PATENT DOCUMENTS

| | | | |
|---|---|---|---|
| 4,499,898 A | | 2/1985 | Knepshield et al. |
| 5,299,357 A | * | 4/1994 | Wonderley et al. ............ 30/339 |
| 5,330,492 A | * | 7/1994 | Haugen ........................ 606/167 |
| 5,344,424 A | | 9/1994 | Roberts et al. |
| 5,391,177 A | * | 2/1995 | Schwartz ...................... 606/167 |
| 5,431,672 A | | 7/1995 | Cote et al. |
| 5,527,329 A | | 6/1996 | Gharibian |
| 5,531,754 A | | 7/1996 | Shackelford, Sr. et al. |
| 5,569,282 A | | 10/1996 | Werner |
| 5,571,127 A | | 11/1996 | DeCampli |
| 5,571,128 A | | 11/1996 | Shapiro |
| 5,620,453 A | | 4/1997 | Nallakrishnan |
| 5,662,669 A | | 9/1997 | Abidin et al. |
| 5,665,099 A | | 9/1997 | Pilo et al. |
| 5,941,892 A | | 8/1999 | Cohn et al. |
| 6,503,262 B1 | | 1/2003 | Edens |
| 6,589,258 B2 | | 7/2003 | Pilo et al. |
| 6,623,499 B1 | | 9/2003 | Andreini et al. |
| 6,645,216 B2 | | 11/2003 | Masury et al. |
| 6,949,109 B2 | | 9/2005 | Iske et al. |
| 6,979,340 B2 | | 12/2005 | Bilenski et al. |
| 2004/0181246 A1 | | 9/2004 | Heppler |

* cited by examiner

*Primary Examiner* — Ryan Severson
*Assistant Examiner* — Jonathan W Miles
(74) *Attorney, Agent, or Firm* — David M. Driscoll, Esq.

(57) ABSTRACT

A multimode instrument assembly (10, 11) configurable for performing a dermatotomy in a percutaneous procedure and further configurable for performing cuts in open surgery includes a pointed blade (68) and a hollow sheath body (18, 200) disposed to encapsulate the pointed blade (68) inside a longitudinal instrument cavity (32) to protect a user. The hollow sheath body (18, 200) is supported for longitudinal translation with respect to the blade (68). The hollow sheath (18) may be positioned and locked at a first position to completely encapsulate the blade (68) inside the instrument cavity (32) for safe handling. Otherwise the hollow sheath body (18, 200) is movable to second and third positions with different lengths of the blade extending out through a front face (23) of the hollow sheath body (18, 200). A compression spring biases the hollow sheath body (18) toward the first safety position. The multimode instrument is primarily intended for making a precise pierce cut with a consistent cut depth and cut length.

18 Claims, 11 Drawing Sheets

SURGICAL INSTRUMENT ASSEMBLY

BACKGROUND OF THE INVENTION

1. Field of the Invention

The present invention relates to a multifunctional scalpel usable as a traditional cutting scalpel and usable for dermatotomy or "skin nick" in percutaneous procedures. In particular, the multifunctional scalpel includes elements for engagement to a guide wire, a scalpel blade for safety, positioning the scalpel blade for piercing, and positioning the scalpel blade for conventional cutting.

2. Description of the Related Art

Percutaneous medical procedures use a needle-puncture of the skin to gain access to an internal location such as a blood vessel, hollow internal cavity, internal organ or other internal location. In many applications, percutaneous medical procedures are preferred over "open" surgery which has more complications. Most percutaneous medical procedures are a variation of the Seldinger technique which involves inserting a hollow needle or trocar into a desired internal location and passing a round-tipped guide wire through the hollow needle until a leading end of the guide wire exits the trocar at the desired internal location. The trocar is then removed by advancing it along the guide wire to its trailing end. While the trocar punctures the skin and installs the guide wire into a blood vessel or other internal cavity, the initial puncture surrounding the guide wire usually needs to be enlarged using a scalpel or other cutting or piercing instrument. After the initial puncture surrounding the guide wire is enlarged, a hollow "sheath" or blunt cannula is passed along the guide wire and inserted through the enlarged puncture wound. The hollow sheath has a larger lumen passing along its axial length and is guided to the desired internal location by the guide wire. Once the sheath is in place, the guide wire is removed and various surgical tools can be installed through the sheath lumen to the desired location.

The procedure for enlarging the initial needle puncture surrounding the guide wire is referred to as a dermatotomy or "skin nick". Ideally, the dermatotomy is substantially coincident with or immediately adjacent to the guide wire entry point. In addition, the depth and size of the dermatotomy may vary for different surgical procedures, different instrument sheath sizes and different body locations. Heretofore the dermatotomy was performed by a surgeon using a conventional scalpel having its cutting blade fully extended and locked in place while held in a free hand and using only visual guidance to position dermatotomy coincident with or immediately adjacent to the guide wire entry point and to make the dermatotomy with a cut depth and length that is suitable for the situation. Even under ideal circumstances, such as with good lighting and a well positioned patient, a dermatotomy performed with a conventional scalpel may not be optimal when it is performed free hand. Moreover, a dermatotomy may need to be performed under non-ideal circumstances, e.g. when performed quickly in an emergency, when preformed in a low light level or when performed with the patient poorly positioned and such procedures are even more difficult to perform optically with a free hand held conventional scalpel.

More recently tools have been developed for guided dermatotomy procedures. In particular, US 2004/0181246 by Heppler, discloses a scalpel configured with a pair of wire guides attached to the scalpel and configured to be guided along the guide wire so that the scalpel blade is guided to the location where the dermatotomy needs to be placed, e.g. coincident with or immediately adjacent to the guide wire entry point. As further disclosed in Heppler, the wire guides can be attached to the scalpel handle, to the scalpel blade, to a plate sandwiched between the scalpel handle and the scalpel blade or to a movable safety sheath that fits over the scalpel blade and partially over the scalpel handle. While the improved scalpel taught by Heppler is usable for both free-hand cutting and guided dermatotomy procedures, the movable safety sheath disclosed by Heppler appears difficult to use. Moreover, it is unclear from the disclosure how the safety shield is attached to the scalpel or moved from multiple operating positions including a depth stop position. Accordingly there is a need for an improved scalpel usable for guided dermatotomy procedures as well as for free hand cutting that provides a more reliable blade retracting mechanism and blade locking mechanism for locking the blade in a plurality of different positions and a more robust mechanism for setting a blade depth stop position for desired cut depths, such as for consistently performing a dermatotomy with a desired length and cut depth.

SUMMARY OF THE INVENTION

The present invention overcomes the problems cited in the prior art by providing improved surgical instrument assemblies (10, 11) that support a surgical instrument (20), such as a scalpel blade, in a fixed position and provide a hollow sheath body (18) that is longitudinally movable with respect to the surgical instrument 20 to alternately encapsulate the surgical instrument 20 inside a second cavity (32), in a safety mode, or expose the surgical instrument through a front face (23), by a desired dimension, when the surgical instrument is being used for surgery. In particular, the sheath body 18, 200 is movable to expose different lengths of the surgical instrument 20 for different applications and can be locked in various positions as required. In addition, the surgical instrument assembly is usable to pierce or make an initial cut in a surgical patient.

In particular the surgical instruments (10, 11) are operable in a pierce mode for performing a dermatotomy procedure by placing the front face (23) of the hollow sheath body (18, 200) against the skin or other surface of a surgical patient and orienting the longitudinal axis of the surgical instrument substantially normal to the skin or other surface of the surgical patient. Next a longitudinal force is applied to the actuator handle in a direction that pushes the handle toward the skin or other surface of a surgical patient. The longitudinal force applied to the handle actuator forces the surgical instrument, in this case a pointed scalpel blade, through the instrument aperture (22) while simultaneously forcing the hollow sheath body to be translated longitudinally toward the handle actuator. The depth of the pierce cut is controlled by limiting the longitudinal travel distance of the hollow sheath body to a travel distance associated with a desired cut depth of the pointed scalpel. This is accomplished by configuring the hollow sheath body and the handle actuator with an interface suitable for limiting the travel distance of the hollow sheath body. In one example, female engaging elements such as a slot arrangement having a plurality of longitudinal slot is formed on the hollow sheath body and engaged with a male engaging element formed on the handle actuator with one longitudinal slot length equal to the desired hollow sheath body travel distance associated with a desired cut depth of the pierce cut. In addition, the sheath body (18, 200) includes a guide wire receiving groove (24) formed on an external surface of the sheath body (18) adjacent to an instrument aperture (22) formed at the front end of the sheath body. The guide wire receiving groove (24) receives a guide wire therein and the guide wire is used to guide the surgical instrument (20), e.g. to guide the scalpel point (82) to a location defined by the guide wire during a pierce cut. Accordingly, the surgical instruments (10, 11) are usable to perform a guided dermatotomy.

The present invention further overcomes problems of the prior art by providing methods for operating a surgical instrument assembly. In particular the methods include positioning a hollow sheath body to a first longitudinal position for encapsulating the surgical instrument inside an instrument cavity and locking the hollow sheath body in the first position when the surgical instrument is not being used for surgery. The method also includes positioning the hollow sheath body to a second longitudinal position for causing the surgical instrument to extend through the instrument aperture with a desired length suitable for performing free hand surgery and locking the hollow sheath body in the second position when the surgical instrument is being used for free hand cutting.

Further methods include passing a suture through a notch opening formed through the hollow sheath body adjacent to the surgical instrument and cutting the suture while the surgical instrument is safely encapsulated inside the instrument cavity.

A further method include performing a guided dermatotomy procedure by first positioning the hollow sheath body in the first longitudinal position with surgical instrument encapsulated safely inside an instrument cavity but without locking the hollow sheath body in the first position. The instrument is then positioned with the front face of the hollow sheath body on a skin or other surface of a surgical patient while orienting the instrument longitudinal axis substantially normal to the skin surface. A user then applies a longitudinal force to the handle actuator pushing the handle toward the patient skin or other surface. This causes the surgical instrument to pierce the skin of the surgical patient to a desire pierce depth while simultaneously forcing the hollow sheath body toward the handle actuator. The depth of the pierce cut is controlled by limiting the longitudinal travel of the hollow sheath body. It is an object of the present invention to provide a scalpel that can be used for both cutting, in open surgery, and for piercing the skin to a desired depth, e.g. for a performing guided dermatotomy procedure.

It is an object of the present invention to provide a scalpel that includes a guide wire receiving groove aligned with a feature of the surgical instrument for receiving a guide wire into the receiving groove and directing the surgical instrument feature to a location defined by the guide wire.

It is a further object of the invention to provide a surgical instrument assembly that includes a sheath body (18, 200) that is movable to a LOCK position for enclosing the surgical instrument (20) inside the sheath body (18, 200) to thereby protect the instrument, to protect the surgical patient, and to protect anyone handling the surgical instrument assembly.

BRIEF DESCRIPTION OF THE DRAWINGS

The features of the present invention will best be understood from a detailed description of the invention and a preferred embodiment thereof selected for the purposes of illustration and shown in the accompanying drawings in which.

DETAILED DESCRIPTION OF THE PREFERRED EMBODIMENT

Figure 1:
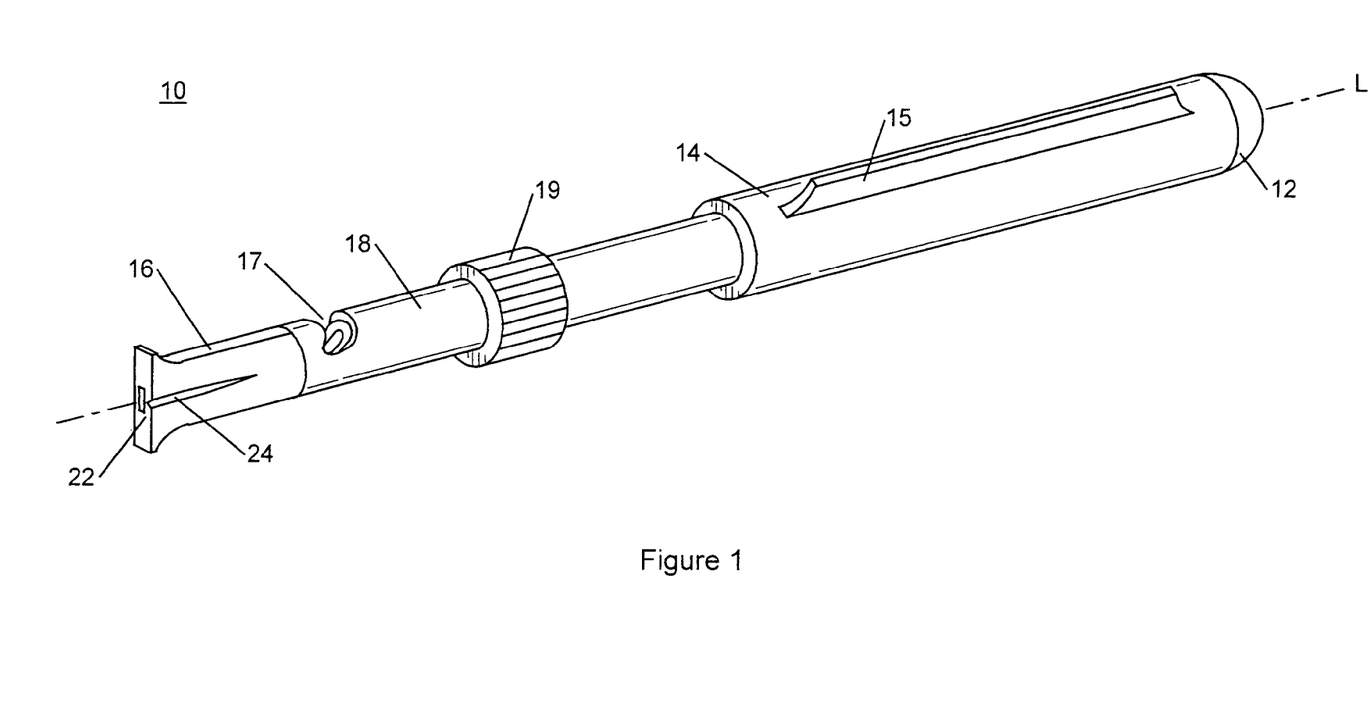
FIG. 1 illustrates a first surgical instrument assembly embodiment shown in an isometric view according to the present invention.
Figure 2:
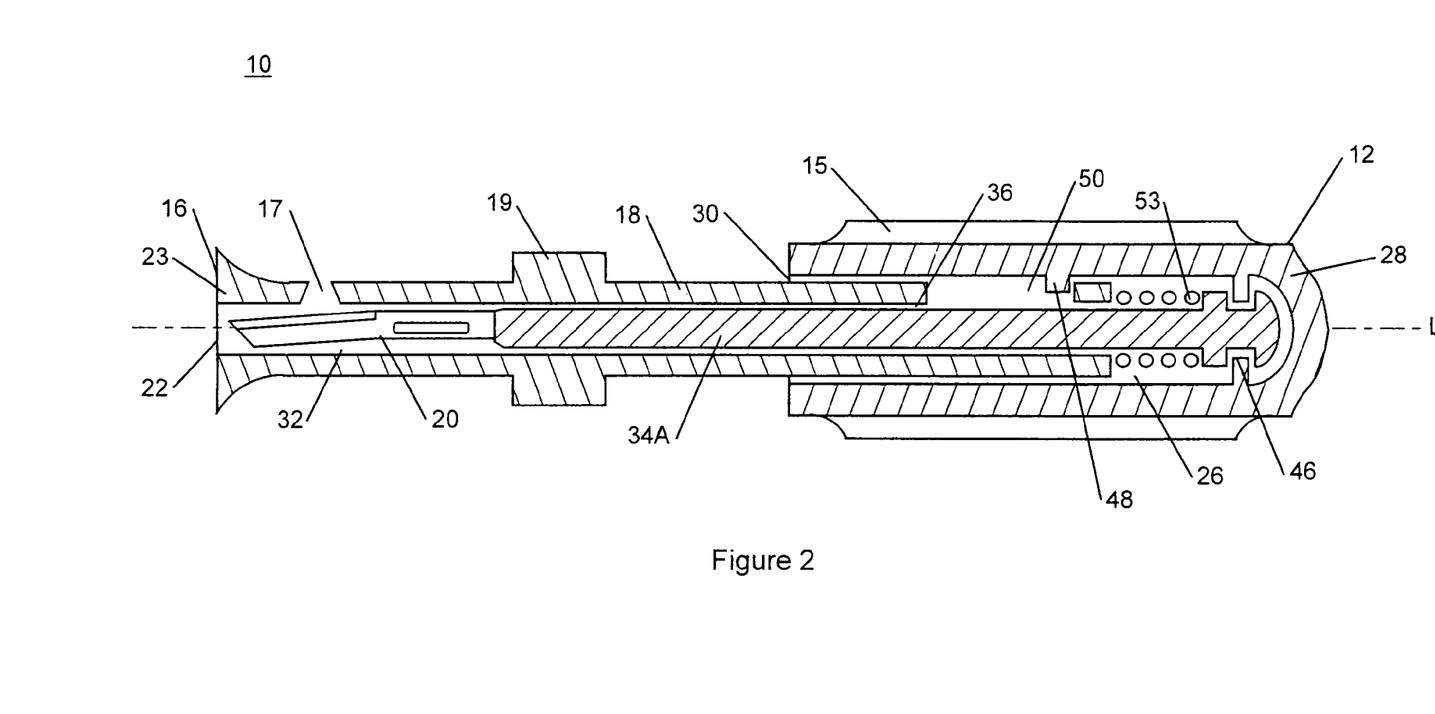
FIG. 2 illustrates the first surgical instrument assembly embodiment shown in section view according to the present invention.

Referring to FIGS. 1 and 2, FIG. 1 depicts an isometric view of a surgical instrument assembly 10, according to a first embodiment of the present invention, and FIG. 2 depicts a section view taken through a longitudinal axis L of the surgical instrument assembly 10. The surgical instrument assembly 10 generally has a back end 12 formed by a handle actuator 14 and a front end 16, opposed to the back end 12, formed by a hollow sheath body 18. A surgical instrument 20, such as a scalpel blade, is fixedly attached to an instrument holder 34A with the instrument holder and scalpel blade 20 supported inside internal hollow cavities of the handle actuator 14 and hollow sheath body 18.

Referring now to FIGS. 1-4, the instrument holder 34A comprises a longitudinal shaft extending along the instrument longitudinal axis L from the front end 16 to the back end 12. At its front end, the instrument holder 34A is configured to support the surgical instrument 20 in a desired orientation. At its mid section the instrument holder 34A includes a longitudinal front shaft portion 62 that guides and supports longitudinal movement of the hollow sheath body 18. At its back end, the instrument holder 34A includes a longitudinal back shaft portion 60 that guides and supports rotation of the handle actuator 14 about the longitudinal axis L.

Generally, the surgical instrument assembly 10 is configured such that the instrument holder 34A and surgical instrument 20 remain substantially fixedly disposed along the longitudinal axis L. The surgical instrument assembly 10 is further configured to translate the hollow sheath body 18 longitudinally toward the back end 12 to expose the surgical instrument 20. The surgical instrument assembly 10 is further configured to rotate the handle actuator 14 about the longitudinal axis L and about the hollow sheath body 18 for locking or unlocking the position of the hollow sheath body 18 at desired positions. As will be detailed below, the hollow sheath body 18 includes a front face 23 and an instrument aperture 22 passing through the front face 23. As the hollow sheath body 18 is longitudinally translated toward the back end, the surgical instrument 20 is exposed through an instrument aperture 22.

The handle actuator 12 includes a pair of diametrically opposed fins 15 extending radially outward from an outer surface of the actuator handle 12 to improve the gripping of the handle actuator 14 to different operating positions. Of course other gripping aids are usable on the handle actuator 12 without deviating from the present invention. Similarly, the hollow sheath body 18 includes a raised diameter 19 to provide a gripping feature on the hollow sheath body 18 to improve gripping during use as a surgical instrument and while translating the hollow sheath body 18 to different operating positions.

In FIGS. 1 and 2, the surgical instrument 10 is shown in a safety or LOCK mode wherein the surgical instrument 20 is completely housed inside the hollow sheath body 18 to protect the surgical instrument 20 from damage and to allow safe storage and handling of the surgical instrument 10. As detailed below, the hollow sheath body 18 may be retracted to exposed the surgical instrument 20 through the aperture 22 and the hollow sheath body 18 may be locked or otherwise held in one or more retracted positions with the surgical instrument 20 exposed for free hand cutting. Alternately, the hollow sheath body 18 may be unlocked in a PIERCE mode wherein the front face 23 is placed against the skin of a surgical patient and the surgical instrument 20 is used to pierce the skin to a desired depth and cut length by pushing the handle actuator 14 longitudinally toward the skin of the surgical patient.

According to a further aspect of the present invention, the hollow sheath body 18 includes a wire receiving groove 24 formed on an external surface thereof. The wire receiving groove 24 is provided to engage with a guide wire such as a wire that may be exiting from a blood vessel or internal cavity of a surgical patient such as during the initial steps of a percutaneous medical procedure. Generally, the guide wire receiving groove 24 is formed on an external surface of the hollow sheath body 18 at the front end 12 front end adjacent to the instrument aperture 22 and the wire receiving groove 24 is aligned with an axis of the surgical instrument 20, such as a cutting blade point, or the like, for guiding the axis of the surgical instrument 20 to a desired location such as toward the initial needle puncture that was used to insert the guide wire into the surgical patient.

According to a further aspect of the present invention, the hollow sheath body 18 includes a notch 17 passing through an outside wall of the hollow sheath body 18 near the front end 16. In particular, the notch 17 is positioned to provide access to a cutting blade of the surgical instrument 20 at times when the surgical instrument 20 is completely encapsulated by the hollow sheath body 18 such as when the hollow sheath body is in the lock position. Accordingly, the cutting blade of the surgical instrument 20 can be used to cut a suture, or the like, without exposing the blade. To cut a suture or the like, the surgical instrument assembly 10 is positioned to receive the suture through a top opening of the notch 17 and tension between the suture and the blade is used to cut the suture at a desired position without exposing the surgical instrument 20. This is a very important safety feature in an operating room environment. The notch 17 has a top opening sized and shaped large enough to allow a suture material to enter the notch 17 and be cut by the blade, but the top opening is formed to prevent the blade from cutting anything that will not fit through the top opening. Accordingly the notch 17 is formed with a top opening dimension of approximately 3 mm or less and preferably about 1 mm.

Referring to FIGS. 1 and 2 the handle actuator 14 comprises an annular body disposed along the longitudinal axis L and encloses a first internal longitudinal cavity 26 extending along the longitudinal axis L and sized to receive a back portion of the hollow sheath body 18 therein. The first internal longitudinal cavity 26 is closed at its back end by an end wall 28 and forms a first aperture 30 at the first longitudinal cavity front end.

Figure 3A:
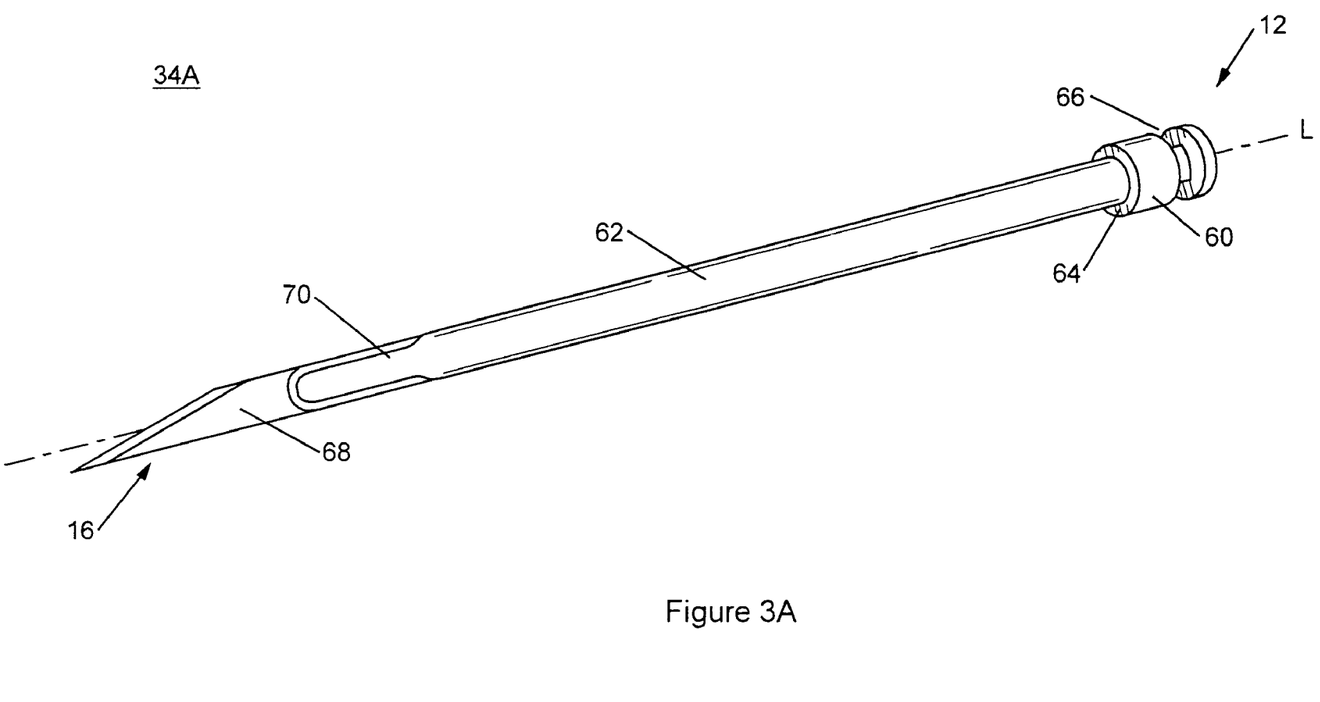
FIG. 3A illustrates a first surgical instrument holder embodiment shown in isometric view according to the present invention.
Figure 3B:
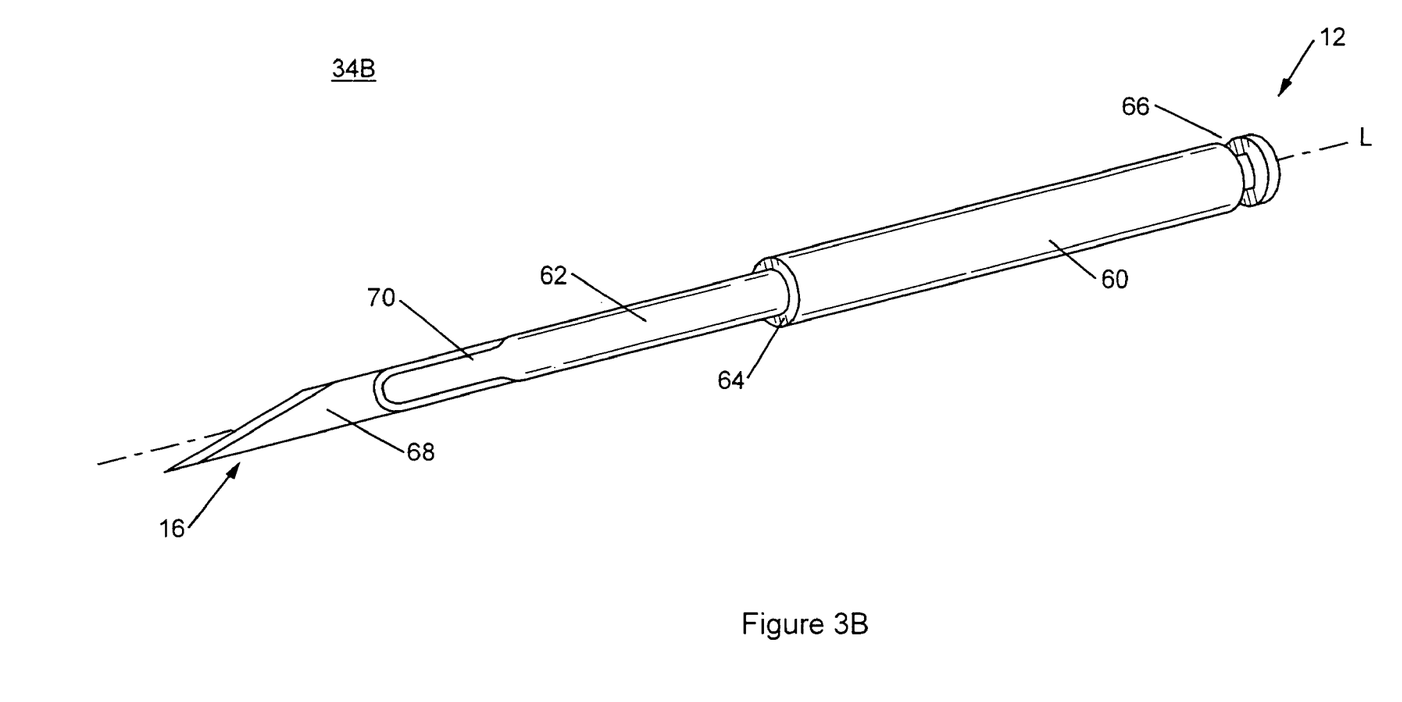
FIG. 3B illustrates a second surgical instrument holder embodiment shown in isometric view according to the present invention.

The hollow sheath body 18 comprises an annular body disposed along the longitudinal axis L and encloses a second internal longitudinal cavity 32, extending along the longitudinal axis L and sized to receive the surgical instrument holder 34A, shown in FIG. 3A, or an alternate embodiment of the surgical instrument holder 34B, shown in FIG. 3B, therein. The second longitudinal cavity 32 forms a second aperture 36 at the second longitudinal cavity back end and the second longitudinal cavity 32 is shaped at the front end as may be required to enclose the surgical instrument 20 and to provide a suitable instrument aperture 22 that allows the surgical instrument 20 to pass through a front wall 23.

Turning now to FIGS. 2, 3A, 3B, 4, and the section views of FIGS. 6A-7C, two different embodiments of surgical instrument holders 34A and 34B are shown in isometric view in FIGS. 3A and 3B respectively. The instrument holder 34A installs in the surgical instrument assembly 10, as shown in the section views of FIGS. 2 and 5A-6C. The instrument holder 34B installs in a second embodiment of a surgical instrument assembly 11, shown in the section the views of FIGS. 7A-7C.

Referring to both FIGS. 3A and 3B the instrument holders 34A and 34B include a pointed scalpel blade 68 attached to front ends thereof. The holders 34A and 34B each comprise a solid substantially uniform diameter elongated front shaft portion 62 disposed along the surgical instrument longitudinal axis L and extending between an instrument holding portion 70 and an increased diameter back shaft portion 60. The back shaft portion 60 has a larger diameter than the front shaft portion 62 and includes features on the back end thereof for interfacing with the handle actuator 14. In particular, the back shaft portion 60 includes a back end formed with an annular groove 66 having a decreased groove diameter axially centered with respect to the longitudinal axis L for interfacing with the handle actuator 14. In addition, a shoulder is formed at the intersection of the back shaft portion 60 and the front shaft portion 62 and the shoulder provides an annular land surface 64. As depicted in FIG. 3A, the first instrument holder 34A has a long front shaft 62 with the annular land surface 64 positioned adjacent to the annular groove 66 near the back end of the instrument holder 34A. As depicted in FIG. 3B, the second instrument holder 34B has a shorter front shaft 62 with the annular land surface 64 approximately positioned at the mid point of the holder 34B.

Figure 4:
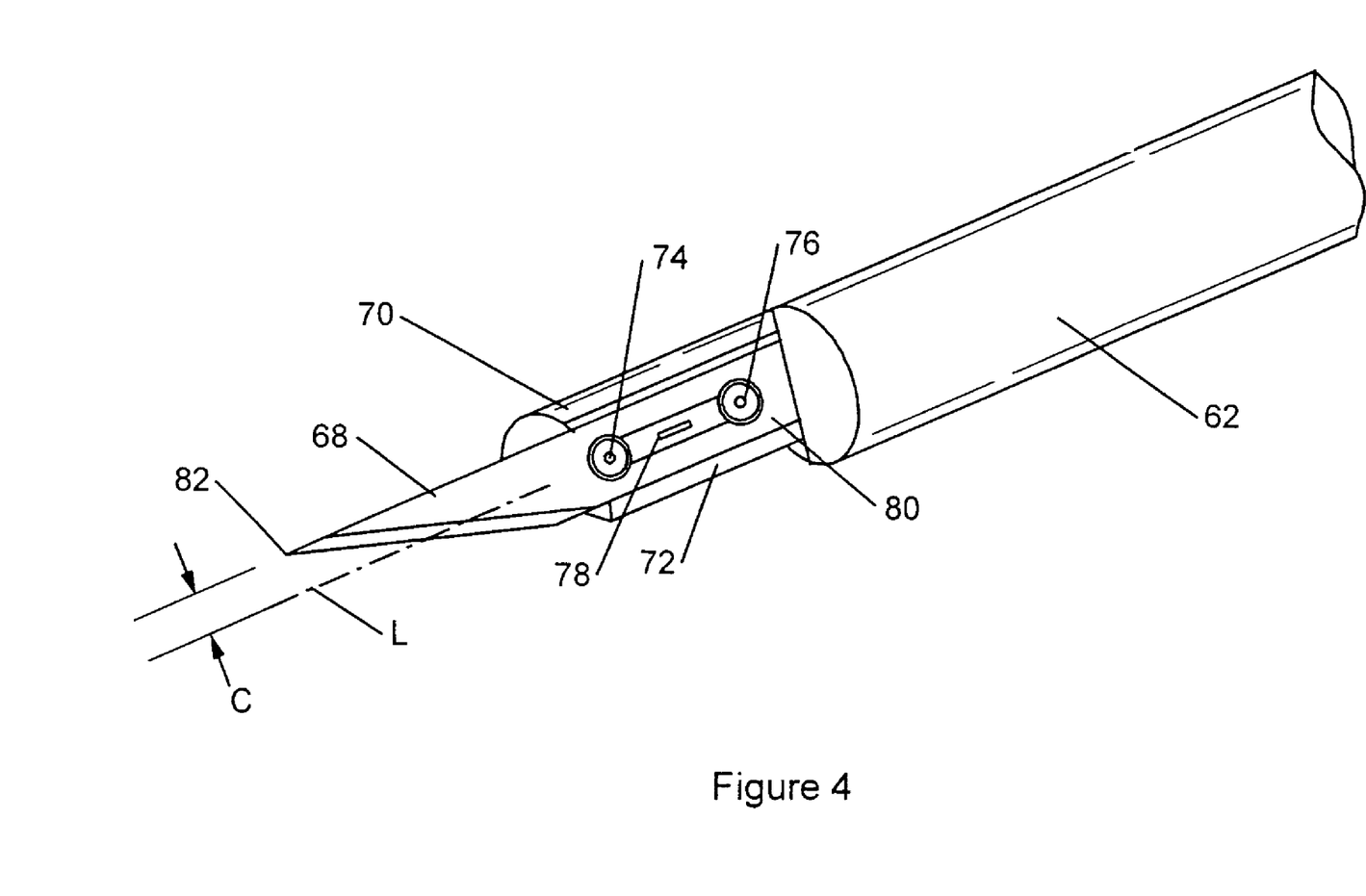
FIG. 4 illustrates a front end of a surgical instrument holder including a pointed scalpel blade attached thereto shown in isometric view according to the present invention.

Referring now to FIG. 4, the instrument holders 34A and 34B each include an instrument holding portion 70, which may be formed integral with the front shaft portion 62, or which may comprise a separate element fixed or removable from the front shaft portion 62. Generally, the instrument holding portion 70 provides features usable to attach a surgical instrument, e.g. the scalpel 68, to the instrument holder 34A or 34B and for orienting the scalpel 68 in a desired orientation and or location with respect to the longitudinal axis L.

In the particular example where the surgical instrument is a conventional scalpel blade 68 formed with a pointed tip 82, the instrument holding end 70 is formed with a flat surface 72 for receiving a shank 80 of the scalpel blade 68, thereon. The flat surface 72 also includes a pair of attaching posts 74 and 76 attached thereto and extending substantially perpendicular from the flat surface 72 to engage with a slotted opening 78. The slotted opening 78 is sized to mate with the attaching posts 74 and 76 and the attaching posts 74 and 76 are positioned and oriented to align an axis of the scalpel blade 68 with the instrument longitudinal axis L. Specifically, the scalpel 68 is oriented coplanar with the longitudinal axis L and the blade point 82 is offset from the longitudinal axis L by a desired offset distance C. In addition, the fit of the slotted opening 78 with the attaching posts 74 and 76 may be an interference or snap fit to mechanically clamp the blade shank 80 in position. Alternately, other clamping or attaching elements may be employed.

According to a preferred embodiment of the present invention, the surgical instrument assemblies 10 and 11 are configured with the scalpel blade 68. However, other scalpel blade types including a rounded scalpel blade, a micro-blade scalpel are usable without deviating from the present invention. Moreover other surgical instruments such as other cutting tools, solid or hollow needles, probes directors, tweezers or forceps, dilators, expanders or retractors are usable without deviating from the present invention. Moreover other medical devices such as electronic or optical instruments, drug delivery devices or the like, that may need to be guided along a guide wire to a wire puncture may be usable in combination with the features and elements of the present invention described herein.

Figure 6A:
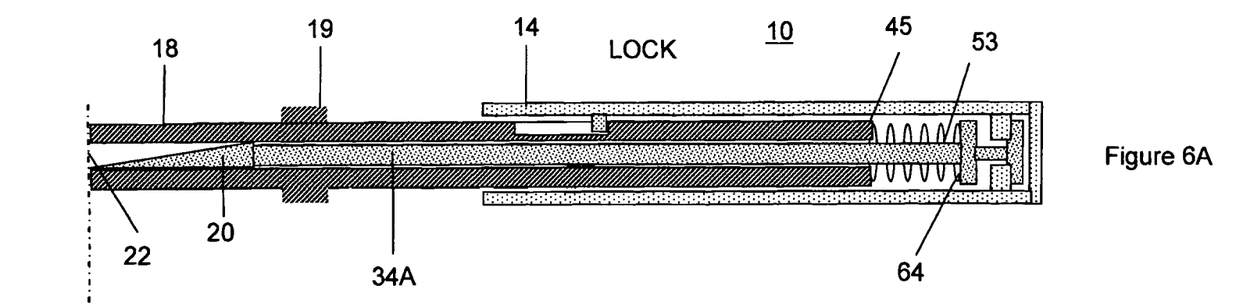
FIG. 6A illustrates a first surgical instrument assembly embodiment shown in section view with a hollow sheath body shown in a LOCK position according to the present invention.
Figure 6B:
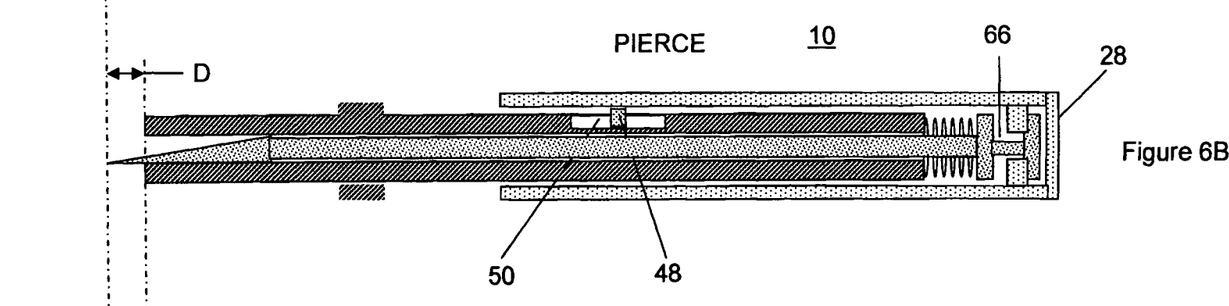
FIG. 6B illustrates the first surgical instrument assembly embodiment shown in section view with a hollow sheath body shown in a PIERCE position according to the present invention.
Figure 6C:
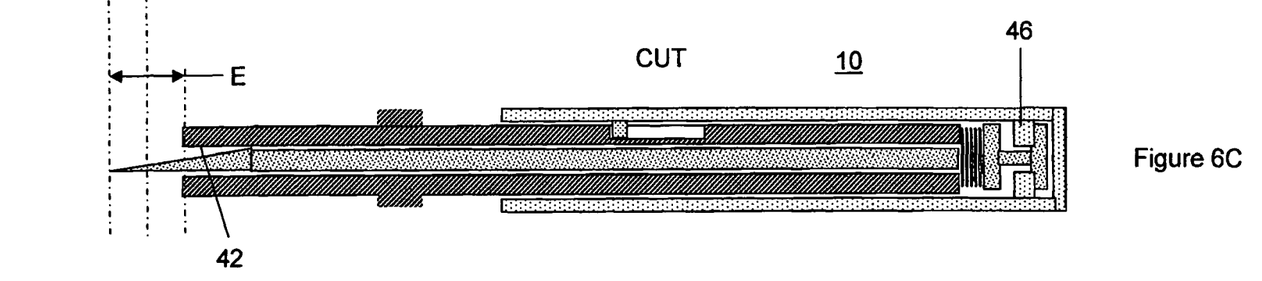
FIG. 6C illustrates the first surgical instrument assembly embodiment shown in section view with a hollow sheath body shown in a CUT position according to the present invention.

Referring to FIGS. 2, 3A and 6A-6C the surgical instrument holder 34A and the attached surgical instrument 20 installs into the hollow sheath body 18 second longitudinal cavity 32 through the second aperture 36. In the example of FIGS. 6A-6C, the second longitudinal cavity 32 has a substantially uniform diameter 42 over its full length for receiving the instrument holder front shaft diameter 62 therein. Alternately, a front portion of the second longitudinal cavity 32 may be shaped as required to receive larger surgical instruments 20 therein. An annular land surface 45 is formed by the back end of the sheath body 18 and is used as a bearing surface for a compression spring 53. The compression spring 53 is a cylindrical spring element open along its longitudinal axis and the spring 53 installs over the instrument holder front end diameter 62 and is captured between the annular land surface 45, formed on the back end of the sheath body 18, and the annular land surface 64 formed on the instrument holder 34A adjacent to the annular groove 46. The compression spring 53 delivers a longitudinal separating force between the instrument holder 34A, which is longitudinally fixed in place, and the sheath body 18, which is longitudinally movable and the spring 53 tends to bias the longitudinal position of the sheath body 18 toward the instrument front end 16.

Referring to FIGS. 3B and 7A-7C, the second embodiment of the surgical instrument assembly 11 includes a second embodiment of a hollow sheath body 200 formed with an internal cavity 202 formed therein. In this embodiment, the surgical instrument holder 34B and surgical instrument 20 install into the longitudinal cavity 202 through the aperture 204. The internal cavity 202 has a substantially uniform front diameter 206, sized to receive the instrument holder front diameter 62 therein, and the second longitudinal cavity 202 has a larger back diameter 208 sized to receive instrument holder back shaft portion 60 therein. A shoulder separating the front diameter 206 and back diameter 208 forms an annular land surface 210 which is used as a bearing surface for a compression spring 52. The compression spring 52 is a cylindrical spring element open along its longitudinal axis and the spring 52 installs over the instrument holder front diameter 62 and is captured between the annular land surface 210 and the annular land surface 64 formed on the instrument holder 34B. The compression spring 52 delivers a longitudinal separating force between the instrument holder 34B, which is longitudinally fixed in place, and the sheath body 200 which is longitudinally movable, and the spring 52 tends to bias the sheath body 200 toward the instrument front end 16.

In each of the example instrument assemblies 10 and 11, internal surfaces of the sheath body 18 and 200, and external surfaces of the instrument holder 34A, 34B as well as internal surfaces of the actuator handle 14 and external surfaces of the hollow sheath body 18 and 200 are fit together with a clearance fit that allows longitudinal translation of the sheath body 18, 200 with respect to the instrument holders 34A or 34B and the actuator handle 18 as well as rotation of the actuator handle 18 about the longitudinal axis L and about hollow sheath body 18 and the clearance fits are made sufficiently small that the surgical instrument 20, instrument holder 34A, 34B sheath body 18, 200 and actuator handle 14 are maintained in substantial alignment with the instrument longitudinal axis L. Specifically, the diametrical clearance between mating elements may range from about 0.25-1.25 mm.

Referring to FIGS. 1, 2, and 6A-7C the back end of the surgical instrument holders 34A and 34B and the back end of the sheath body 18 or 200 install into the handle actuator first longitudinal cavity 26 by passing through the actuator handle front end aperture 30. The actuator handle 14 includes an annular lip 46 formed substantially opposed to the end wall 28. The annular lip 46 reduces the diameter of the first longitudinal cavity 26 and is axially centered with respect to longitudinal axis L. The annular lip 46 is provided to engage with the instrument holder annular groove 66 by pressing or otherwise placing the back end of the instrument holder back shaft 60 into engagement with the annular lip 46. Alternately the handle actuator 14 may be configured with two longitudinal half sections that engaged with the annular groove 66 at assembly and that may be bonded or otherwise fastened together at assemble. The engagement of the annular lip 46 with the annular groove 66 prevents longitudinal movement of the instrument holder 34A or 34B and the handle actuator 14. The annular lip 46 and annular groove 66 are each sized to fit together with a clearance fit. The clearance fit is made sufficiently large that the actuator handle 14 can be rotated about the longitudinal axis L with respect to the instrument holder 34A or 34B. Meanwhile, the clearance fit between the annular lip 46 and annular groove 66 is small enough to maintain the instrument holder back shaft 66 in substantial alignment with the instrument longitudinal axis L. For example, the diametrical and axial clearances between the annular lip 46 and annular groove 66 may range from about 0.25-1.25 mm. Alternately, a snap ring or other suitable fastener may be used instead of the annular lip 46 and installed through an annular groove formed through the handle actuator 14.

Referring now to FIGS. 2, and 5A-6C, the handle actuator 14 includes a fixed pin 48 or other male engaging element protruding substantially axially inward from an inner wall of the first longitudinal cavity 26. The pin 48 may be integrally formed with the handle actuator 14, such as molded in place, or the pin 48 may comprise a set screw, or the like, threaded through a wall of the first longitudinal cavity 26. The sheath body 18, 200 includes a female engaging element 50, such as an arrangement of slotted elements described below for receiving the male engaging element 48 therein. Specifically, the female engaging element 50 passes fully or partially through an outer wall of the sheath body 18 and is sized to movably receive the fixed pin 48 therein with a minimum of clearance between the pin and female engaging element 50. The longitudinal position of the pin 48 is fixed with respect to the actuator handle end wall 28 such that rotation of the actuator handle 14 rotates the pin 48 in a circular path around the longitudinal axis L at a fixed longitudinal position. By engaging with the slot 50, the rotation of the actuator handle 18 and therefore the pin 48 about the longitudinal axis L may be used engage the pin 48 with various features of the female engaging element 50, such as detents and longitudinal slot sections, in order to select a desired longitudinal position of the sheath body 18, 200. Accordingly, the female engaging element 50 may be formed with various longitudinal slots, and with detents which when engaged with the pin 48 allow longitudinal translation of the hollow sheath body 18, 200 and may hold the sheath body in desired longitudinal positions. In addition, the pin 48 may be supported on a flexure extending between the pin 48 and the handle actuator 14 for allowing the pin 48 to flex axially away from the longitudinal axis L during assembly of the instrument. Alternately, the entire actuator handle 14 may be constructed as a flexure with flexible elements formed integral with the actuator handle to flexibly expand its inside diameter during assembly to allow the pin 48 to pass over the hollow sheath body 18, 200 before engaging with the female engaging element 50.

According to the invention, the surgical instrument assembly 10 and 11 are assembled by installing the spring 52 or 53 onto the instrument holder front shaft 62, installing the surgical instrument 20 onto the instrument holding portion 70 and then installing the surgical instrument holder 34A, 34B into the sheath body second longitudinal cavity 32, 202 through the sheath body second aperture 36, 204. The back end of the surgical instrument holder 34A, 34B and the back end of the sheath body 18, 200 are then installed into the actuator handle first longitudinal cavity 26 through the handle actuator first aperture 30 and pushed longitudinally from the front end 16 to engage the instrument holder annular groove 66 with the handle actuator annular lip 46. The handle actuator 14 is then rotated about the longitudinal axis L until the male engaging element or fixed pin 48 is engaged with the female engaging elements or arrangement of slotted elements 50.

Figure 5A:
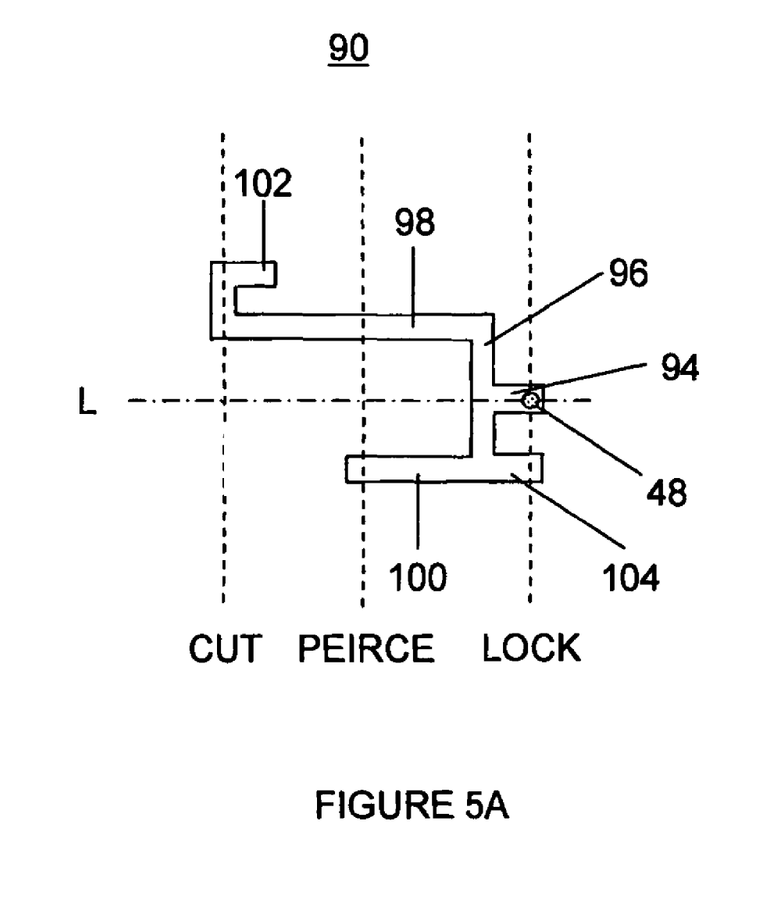
FIG. 5A illustrates a first arrangement of slotted elements shown in plan view and usable as a female engaging element according to a preferred embodiment of the present invention.
Figure 5B:
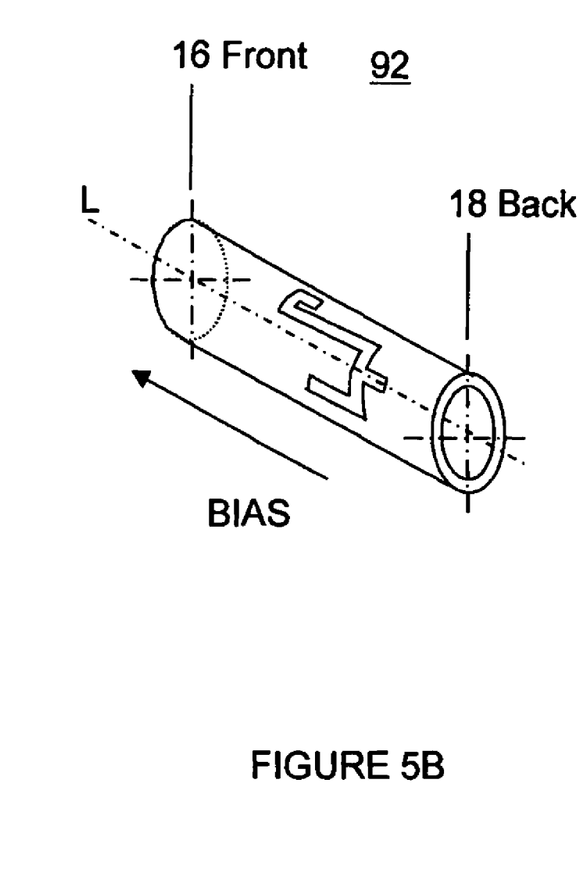
FIG. 5B illustrates the first arrangement of slotted elements usable as a female engaging element shown on a cylindrical wall according to the present invention.

Referring now to FIGS. 5A and 5B, a preferred embodiment of a female engaging slot arrangement 90 is shown in plan view in FIG. 5A and shown in FIG. 5B disposed on a hollow cylindrical element 92. The element 92 corresponds with a cylindrical mid section of the hollow sheath body 18 or 200. The female engaging slot arrangement 90 may comprise slotted openings passing completely through the thickness of an outer annular wall of the cylindrical element 92 or the slotted openings may have a slot depth that is less than the wall thickness of the cylindrical element 92 but deep enough to engage with the male engaging element 48. The surgical instrument longitudinal axis L is shown coincident with the longitudinal axis of the hollow cylindrical element 92 and the cylindrical element front end and back end correspond with the surgical instrument front end 16 and back end 12 as described above.

According to a preferred embodiment of the present invention, the male engaging pin 48 engages with the female engaging slot arrangement 90 while the hollow sheath body 18, 200 is continuously biased toward the front end 16 by the compression springs 52, 53. In the LOCK position, the hollow sheath body 18, 200 is at its front most position where it encapsulates the surgical instrument 20. In the Lock position, the male engaging pin 48 is engaged with a back detent slot 94. To unlock the surgical instrument assembly, a user grasps the hollow sheath body gripping region 19 and the handle actuator 14 and pulls the sheath body 18, 200 toward the instrument back end 18 until the pin 48 is engaged with the cross slot section 96. Thereafter the handle actuator 14 can be rotated clockwise, as viewed from the back end 18, to engage with a cut slot 98. Alternately, the handle actuator 14 may be rotated counter-clockwise to engage with a pierce slot 100.

Figure 7A:
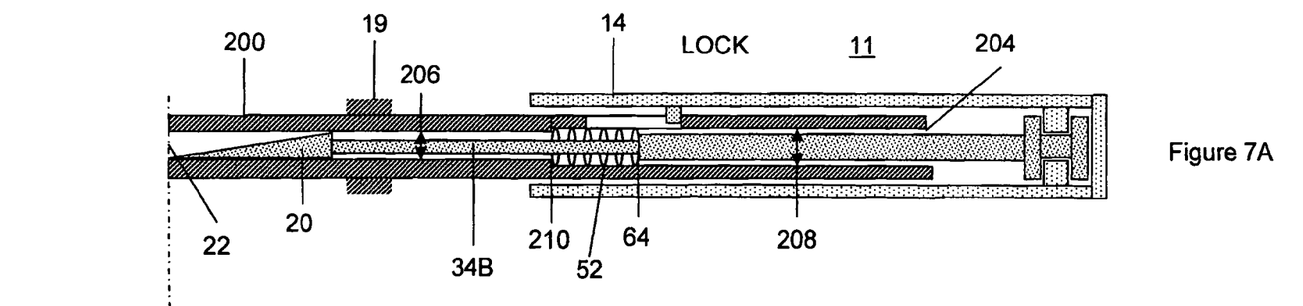
FIG. 7A illustrates a second surgical instrument assembly embodiment shown in section view with a hollow sheath body shown in a LOCK position according to the present invention.
Figure 7B:
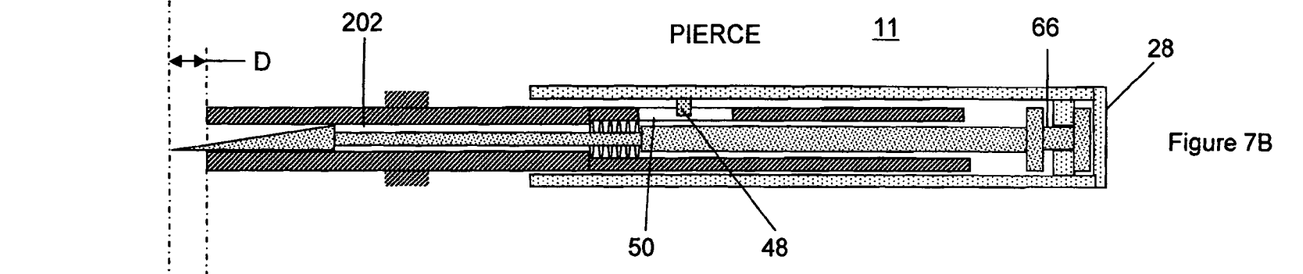
FIG. 7B illustrates the second surgical instrument assembly embodiment shown in section view with a hollow sheath body shown in a PIERCE position according to the present invention.
Figure 7C:
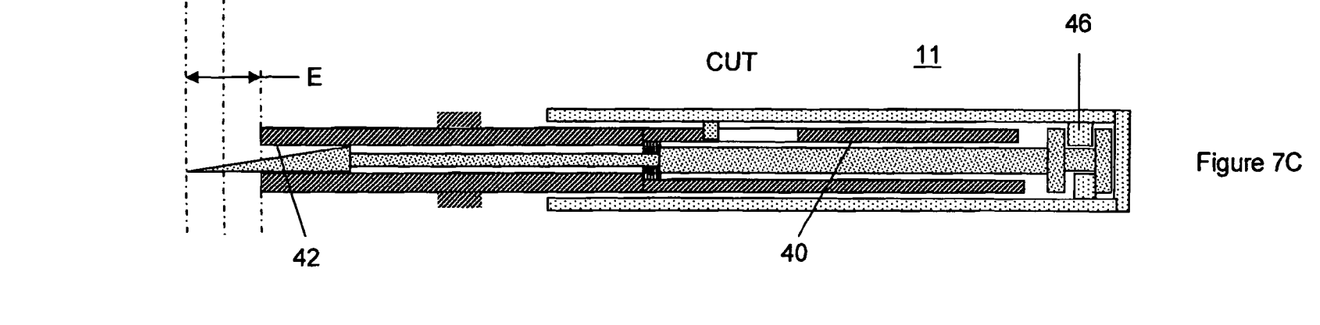
FIG. 7C illustrates the second surgical instrument assembly embodiment shown in section view with a hollow sheath body shown in a CUT position according to the present invention.

If engaged with the cut slot 98, the user pulls the sheath body 18, 200 further toward the instrument back end 18, and then further rotates the handle actuator 14 clockwise to engage the pin 48 with a cut detent slot 102. Once engaged in the cut detent slot 102, the spring bias force pushes the hollow sheath body forward against the male engaging pin 48 thereby locking the hollow sheath body 18, 200 in a CUT position. The cut position is shown in FIGS. 6C and 7C which show the surgical instrument 20 extending out from the instrument aperture by a distance E.

If rotated to the pierce slot 100, the bias force pushes the hollow sheath body forward to engage the male engaging pin 48 with a pierce detent 104 and hold it in place therein. The pierce detent 104 is co-aligned with the pierce slot 100. The pierce detent 104 is configured to position the sheath body substantially in its forward most position which encapsulates the surgical instrument 20. To use the surgical instrument in the PIERCE mod, the user places the instrument front face 23 against the skin of a surgical patient with the instrument longitudinal axis L substantially normal to the skin surface. The user uses the wire receiving groove 24 with a guide wire 21 exiting from the surgical patient to position the front wall or face 23 for making a piece cut adjacent to the where the guide wire 21 exits a blood vessel or internal cavity of the surgical patient. The user then pushes the handle actuator 14 substantially longitudinally thereby driving the instrument holder and surgical instrument toward the skin of the surgical patient where the surgical instrument 20 pierces the skin proximate to the guide wire. In response to the user pushing the handle actuator 14 substantially longitudinally, the hollow sheath body 18 remains stationary while the male engaging pin 48 moves along the length of the pierce slot 100. Accordingly, the depth of the piercing cut is controlled by the length of the pierce slot 100 which stops the travel of the handle actuator and surgical instrument holder when the male engaging pin 48 impacts the front end of the piercing slot 100.

After completing a piercing cut, the bias force of the compression spring 52, 53 acts to separate the handle actuator 14 and sheath body 18, 200 thereby retracting the surgical instrument 20 from the surgical patient until the male engaging pin 48 is once again in the pierce detent 104 and the handle actuator, surgical instrument holder 34A or 34B and the surgical instrument 20 have moved to a position where the surgical instrument is again encapsulated inside the hollow sheath body 18, 200. In the PIERCE mod, the surgical instrument 20 moves to extend out from the front face 23 by a distance D shown in FIGS. 6B and 7B. The distance D is controlled by the length and position of the pierce slot 100.

Figure 8:
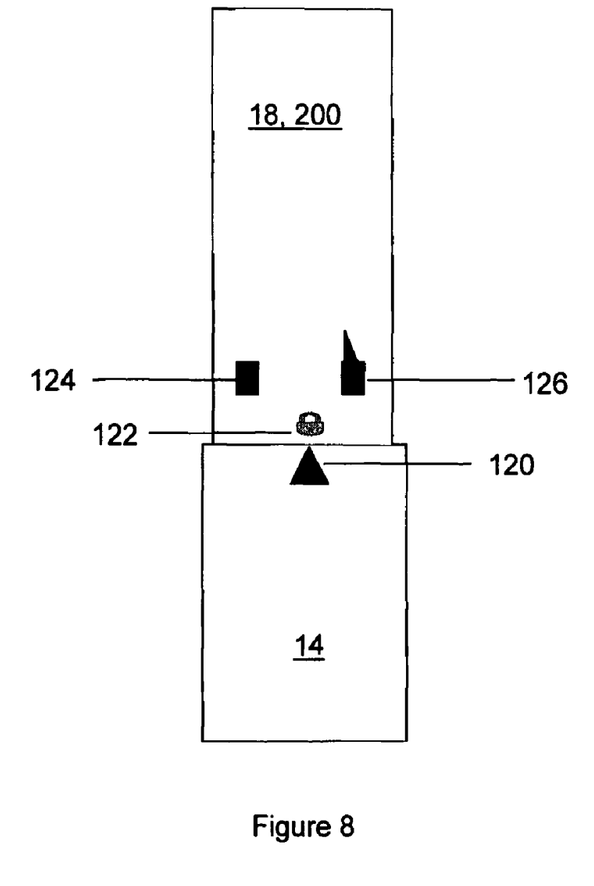
FIG. 8 schematically illustrates markings on outside surfaces of the handle actuator and the hollow sheath body for indicating configurations of the surgical instrument.

Referring now to FIG. 8, example markings or other indicia usable on outside surfaces of the surgical instrument 10, 11 are shown schematically. An single arrow head 120 is shown on an outside surface near a front edge of the handle actuator 14 centered on the longitudinal axis L. The arrow head 120 points toward a lock symbol 122 shown on an external surface of the hollow sheath body 18, 200 and adjacent to an edge of the handle actuator 14. The arrow 120 and lock symbol 122 are positioned such that with the arrow head 120 pointing toward the lock symbol 122, the handle actuator 14 and hollow sheath body 18, 200 are positioned in the LOCK position.

Two additional symbols are shown on the outside surface of the hollow sheath body to the left and right of the lock symbol 122. The symbol 124 is a pierce symbol and the symbol 126 is a cut symbol. When the handle actuator 14 is rotated to align the male engaging pin 48 with the pierce 100 or pierce engaging slot 104 the arrow head 120 points toward the pierce symbol 124. When the handle actuator 14 is rotated to align the male actuator pin 48 with the cut slot 98 or the cut detent 102, the arrow head 120 points toward the cut symbol 126. Any of the symbols 120-126 may be marked or decaled onto outside surface of the handle actuator or the hollow sheath body or the symbols 120-126 may be formed as surface features such as raised or recessed surfaces.

Figure 9A:
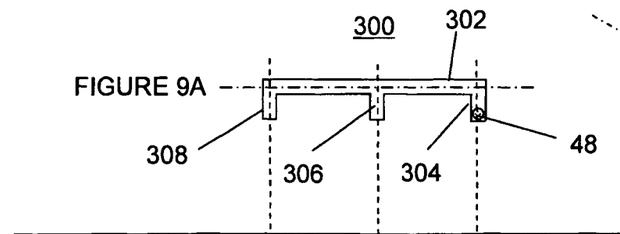
FIG. 9A illustrates a second arrangement of slotted elements shown in plan view and usable as a female engaging element according to the present invention.
Figures 9B, 10B:
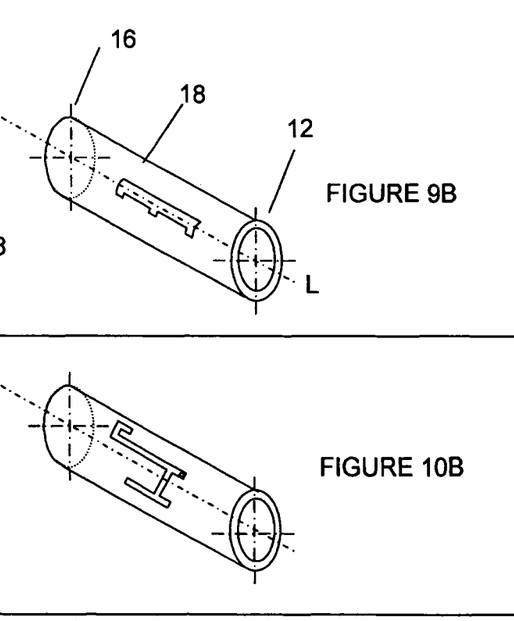
FIG. 9B illustrates the second arrangement of slotted elements usable as female engaging elements shown on a cylindrical wall according to the present invention.
FIG. 10B illustrates the third arrangement of slotted elements usable as female engaging elements shown on a cylindrical wall according to the present invention.
Figure 10A:
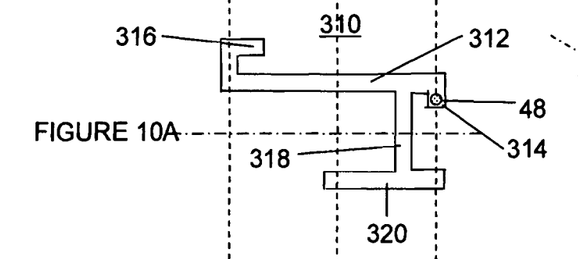
FIG. 10A illustrates a third arrangement of slotted elements shown in plan view and usable as a female engaging element according to the present invention.
Figure 11A:
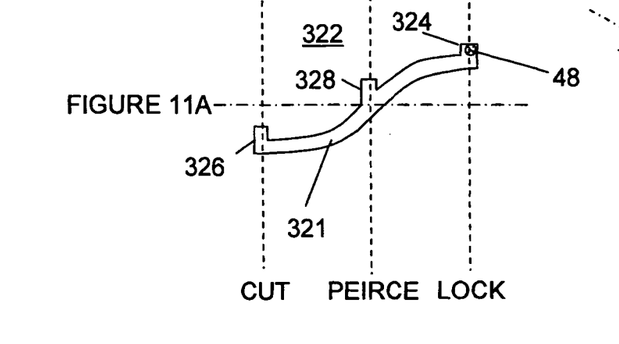
FIG. 11A illustrates a fourth arrangement of slotted elements shown in plan view and usable as a female engaging element according to the present invention.

Referring now to FIGS. 9A-11B, three different configurations of female engaging slot arrangements 300, 310, 322 are shown in a plan view in FIGS. 9A, 10A and 11A. The female slot arrangements 300, 310 and 322 are also shown disposed on a hollow cylindrical element 93 in FIGS. 9B, 10B and 11B. These alternative slot embodiments are shown to illustrate additional methods and configurations for longitudinally translating the hollow sheath body 18, 200 to alternately expose the surgical element 20 through the instrument aperture 22 or to encapsulate the surgical element 20 inside the hollow sheath body 18, 200 according to further aspects of the present invention.

In the longitudinal slot arrangement 300, shown in FIGS. 9A and 9B the slot arrangement 300 includes a longitudinal slot 302 and three detents 304, 306 and 308. A lock detent 302 corresponds to the LOCK position such that when the male engaging pin 48 is engaged with the lock detent 302 the hollow sheath body 18, 200 is positioned to encapsulate the surgical instrument 20 and held in place. A cut detent 308 corresponds the CUT position such that when the male engaging pin 48 is engaged with the cut detent 308 the hollow sheath body 18, 200 is positioned to expose the surgical instrument 20 by the distance E from the front face 23 as shown in FIGS. 6C and 7C and held in place. In addition, an intermediate detent 306 is provided such that when the male engaging pin 48 is engaged with the intermediate detent 306 the hollow sheath body 18, 200 is positioned to expose the surgical instrument 20 by less than the distance E from the front face 23, such as a distance D shown in FIGS. 6B and 7B and held in place.

In the slot arrangement 310, shown in FIG. 10A a longitudinal slot 312 includes a lock detent 314 at its back end and a cut detent 316 at it front end. The longitudinal slot 312 is used to move the hollow sheath body 18, 200 between the LOCK position, shown in FIGS. 6A and 7A, and the CUT position, shown in FIGS. 6C and 7C. A cross slot section 318 allows the male engaging pin 48 to engage with a pierce slot 320 when the handle actuator 14 is rotated. With the male engagement pin 48 engaged with a back end of the pierce slot 320 the hollow sheath body 18 is position to encapsulate the surgical instrument 20 and the hollow sheath body is movable to allow the surgical instrument assembly to operate in the PIERCE mod as described above.

Figure 11B:
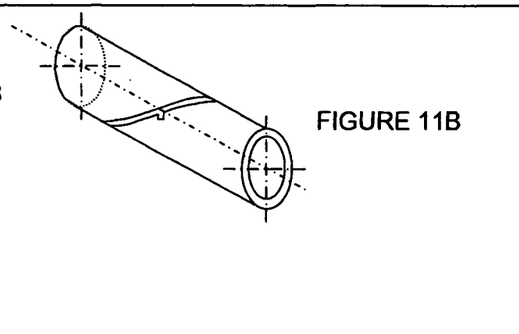
FIG. 11B illustrates the fourth arrangement of slotted elements usable as female engaging elements shown on a cylindrical wall according to the present invention.

In the slot arrangement 322, shown in FIGS. 11A and 11B, includes a spiral slot 321, a lock detent 324, a cut detent 326 and a middle detent 328. With the male engaging pin 48 engaged with the lock detent 324 the surgical instrument 20 is encapsulated by the hollow sheath body 18, which is held in place. With the male engaging pin 48 engaged with the cut detent 326, the surgical instrument extends out from the sheath body by a distance E as shown in FIGS. 6C and 7C, and the sheath body is held in place. With the male engaging pin 48 engaged with the middle detent 328 the surgical instrument extends out from the sheath body by less than the distance E, such as a distance D shown in FIGS. 6B and 7B, and the sheath body is held in place.

Figure 12:
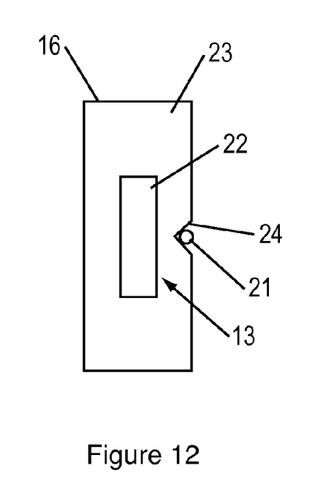
FIG. 12 illustrates a front end view of the surgical assembly showing a bridge between the instrument aperture and the guide wire receiving grove, and a guide wire positioned in the groove.
Figure 13A:
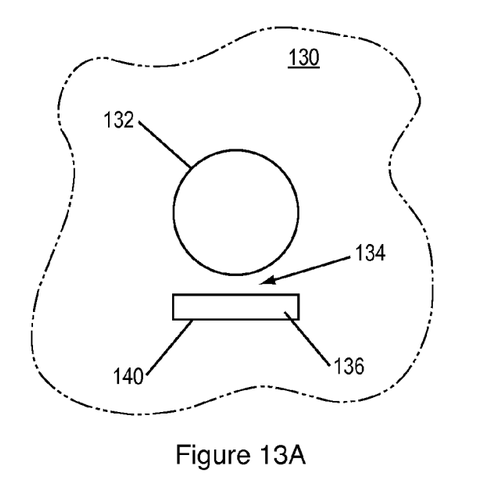
FIG. 13A illustrates a hole for insertion of a guide wire, dilator or catheter, and a pierce cut spaced from the hole by a patient bridge area having a spacing determined by the surgical instrument assembly according to the present invention.

Referring to FIG. 12 and FIG. 13A, FIG. 13A illustrates a hole or puncture 132 in a patient 130 for insertion of the guide wire 21, a dilator or a catheter, and a pierce cut 136 is spaced from the hole 132 by the bridge 13. The surgical instrument assembly 10 is positioned normal or perpendicular to the surface of the surgical patient adjacent to the existing guide wire 21 extending from the hole or puncture 132 on the surgical patient 130 so that the front face 23 rests on the surface of the surgical patient. The groove 24 receives the guide wire 21 and the pierce mode of the surgical instrument assembly 10 is activated, resulting in a cut 136 approximately 0.5 mm from the edge of the puncture or hole 132 from where the guide wire 21 is exiting. The resulting space between the inner edge of the cut 136 facing the hole 132 and the edge of the hole 132 is referred to as the patient bridge area 134 which plays an important role in preventing infections in the patient 130. As noted above the bridge width area 134 resulting from the piercing mode of the present instrument assembly 10 is approximately 0.5 mm in the present embodiment, but this may be varied depending on experiences with patients.

Referring to FIG. 12, the front end 16 of the surgical instrument assembly 10 is shown comprising the front wall or face 23, the instrument aperture 22, a groove 24 for receiving a guide wire, a guide wire 21, and a bridge 13 which is the distance between the right edge of the instrument aperture 22 and the tip of the groove 24 facing the aperture 22. The groove 24 may be V-shaped as shown in FIG. 12 or it may be other known shapes such as U-shaped. In the present embodiment the width of the bridge 13 is approximately 0.5 mm. However, one skilled in the art will recognize that the width of the bridge 13 may be varied depending on experiences with patients for reducing bleeding or infection. As previously discussed, the groove 24 receives a guide wire 21 that may be exiting from a blood vessel or internal cavity of a surgical patient.

Figure 13B:
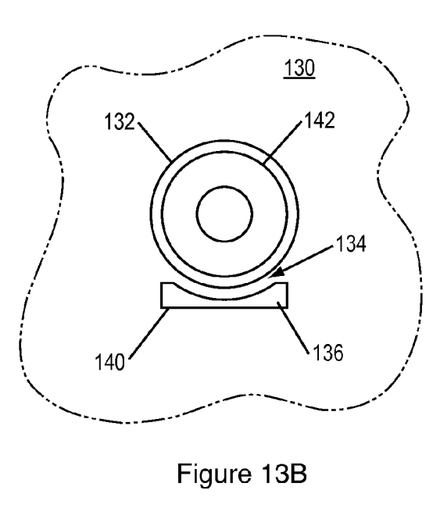
FIG. 13B illustrates an expanded hole of FIG. 13A with a dilator partially inserted therein causing the patient bridge area to encroach into the pierce cut opening and still providing a seal against the dilator.

Referring to FIG. 13B, FIG. 13B illustrates the hole of FIG. 13A expanded with a dilator 142 partially inserted therein causing the patient bridge area 134 to expand due to its elasticity into the area of the pierce cut 136. The surface of the patient bridge area 134 against the dilator acts as a sling and continues to provide a seal to prevent fluids from escaping from the hole 132.

Figure 13C:
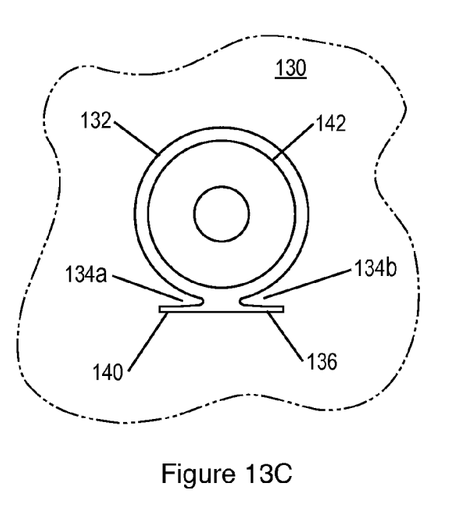
FIG. 13C illustrates the expanded hole of FIG. 13B with the dilator 142 fully inserted therein causing the patient bridge area to separate, and the outer skin of the pierce cut providing a seal against the dilator.

Referring to FIG. 13C, FIG. 13C illustrates the hole 132 of FIG. 13B with the dilator 142 inserted when a dermatotomy is too close to the hole 132 therein causing the patient bridge area 134 to widen and separate into portions 134a and 134b. Eventually, parts 134a and 134b disappear and are absorbed into a larger open area 136, 140 where bleeding or infection can occur. A pierce cut made contiguous to the guide wire, or too close to the guide wire, is a common outcome of using a standard scalpel and ordinary skill of the art. The surgical instrument assembly 10 ensures that the patient bridge area 134 is adequate in size to remain intact when the dilator is inserted. The use of the surgical instrument assembly 10 to produce the accurate pierce cut 136 produces the approximate 0.5 mm bridge between the hole 132 and the pierce cut 136 which cooperates in providing a seal around the dilator or catheter without leaving any open area where bleeding or infection could occur. FIG. 13B represents the desired outcome using the surgical instrument 10. FIG. 13C represents an undesirable, yet common outcome using a standard scalpel and ordinary skill of the art.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications, e.g. as a surgical instrument assembly, those skilled in the art will recognize that its usefulness is not limited thereto and that the present invention can be beneficially utilized in any number of environments and implementations where it is desirable to enclose an instrument inside a sheath and to guide the instrument to a desired location during use. Accordingly, the claims set forth below should be construed in view of the full breadth and spirit of the invention as disclosed herein.

What is claimed is:

1. A multimode instrument assembly for standardizing a dermatotomy procedure having a longitudinal axis, a front end and a back end comprising:

an instrument holder extending along the longitudinal axis having an instrument holding portion disposed at the front end, a back shaft portion disposed at the back end, and a front shaft portion extending between the instrument holding portion and the back shaft portion;

a blade fixedly attached to the instrument holding portion;

a hollow sheath body comprising an annular wall surrounding a second longitudinal cavity for encapsulating the blade therein and for interfacing with the front shaft portion to movably support the hollow sheath body for longitudinal translation with respect to the front shaft portion and the blade;

a handle actuator comprising an annular wall surrounding a first longitudinal cavity for movably receiving the hollow sheath body therein and for interfacing with the back shaft portion to support the handle actuator with respect to the back shaft portion and the hollow sheath body;

said hollow sheath body being movable between multiple positions including a piercing position for making a predetermined accurate pierce cut in a patient, further including means disposed in said hollow sheath body and said handle actuator for exposing said blade a constant piercing length, depth, and location at the front end;

said hollow sheath body extending distally along opposed side walls that terminate in a front face of the hollow sheath body that is for resting on the surface of a surgical patient, said front face extending substantially transverse to the longitudinal axis of the instrument assembly, said front face having an aperture therein through which the blade extends in the piercing position thereof; and said front end including at least one guide wire receiving groove for receiving therein a guide wire, said groove being an indentation extending into and along a first side wall of the opposed side walls of said hollow sheath body, said groove having a predetermined depth therealong and extending continuously from a location along the longitudinal axis that is proximal to the end face to terminate at the end face, the depth of said groove being positioned a predetermined distance away from said aperture in said front face to provide for forming a bridge between the aperture and the groove.

2. The multimode instrument assembly of claim 1 further comprising a compression spring disposed on the front shaft portion between the hollow sheath body and the back shaft portion for generating a biasing force that biases the hollow sheath body toward the instrument front end.

3. The multimode instrument assembly of claim 2 wherein the hollow sheath body has a first longitudinal position, a second longitudinal position, and a third longitudinal position, said third longitudinal position being the piercing position, and said hollow sheath body is movable between said first longitudinal position that encapsulates the total blade inside the second longitudinal cavity and said second longitudinal position that causes a first desired length of the blade to be exposed at the front end.

4. The multimode instrument assembly of claim 3 wherein the first desired length is suitable for performing free hand surgery.

5. The multimode instrument assembly of claim 4 wherein the first desired length is in the range of 1.25-7.0 mm.

6. The multimode instrument assembly of claim 3 further comprising elements disposed between the hollow sheath body and the handle actuator for locking the hollow sheath body in the first longitudinal position.

7. The multimode instrument assembly of claim 6 further comprising elements disposed between the hollow sheath body and handle actuator for locking the hollow sheath body in the second longitudinal position.

8. The multimode instrument assembly of claim 3 further comprising a notch passing through the hollow sheath body for providing external access to the blade when the hollow sheath body is in the first longitudinal position.

9. The multimode instrument assembly of claim 1 wherein said groove is elongated, has a length less than the length of the hollow sheath body, and extends generally in the same direction as the longitudinal axis.

10. The multimode instrument assembly of claim 1 wherein moving the hollow sheath body between the first longitudinal position and the third longitudinal position causes said constant piercing length of the blade to be exposed at the front end.

11. The multimode instrument assembly of claim 1 wherein exposing said blade a constantly piercing length, depth, and location enables making said dermatotomy in a percutaneous procedure.

12. The multimode instrument assembly of claim 11 wherein said predetermined fixed piercing length is in the range of 0.25 mm-1.25 mm.

13. The multimode instrument assembly of claim 1 wherein the guide wire receiving groove is positioned to guide the blade to make the dermatotomy substantially coincident with a puncture surrounding the guide wire.

14. The multimode instrument assembly of claim 1 wherein said groove is a substantially V-shaped groove.

15. The multimode instrument assembly of claim 1 further comprising a notch passing through the hollow sheath body for providing external access to the blade when the hollow sheath body is in the first longitudinal position.

16. The multimode instrument assembly of claim 1 wherein the handle actuator is rotatably attached to the back shaft portion for rotation about the longitudinal axis with respect to the back shaft portion and the hollow sheath body, and further wherein said handle actuator having a male engaging element disposed substantially normal to the annular wall and protruding into the first longitudinal cavity;

wherein the hollow sheath body has a first longitudinal position, a second longitudinal position, and a third longitudinal position, said third longitudinal position being the piercing position;

wherein the hollow sheath body includes a female engaging element comprising a slot arrangement formed on the annular wall thereof to engage with the male engaging element such that the hollow sheath body is movable to one of the first, the second and the third longitudinal positions; and, wherein the handle actuator is rotatable to lock the hollow sheath body at one of the first and the second longitudinal position.

17. The multimode instrument assembly of claim 16 wherein the slot arrangement is further formed with slot elements configured to allow movement of the hollow sheath body from the lock first longitudinal position to the piercing third longitudinal position when the front face is placed against the skin of said patient and a longitudinal force is applied to the actuator handle.

18. The multimode instrument assembly of claim 1 further comprising symbols formed on external surfaces of the hollow sheath body and the handle actuator for indicating operating modes of the surgical instrument assembly.

* * * * *